United States Patent [19]

Leonard

[11] 4,306,865
[45] Dec. 22, 1981

[54] DENTAL HANDPIECE REDUCTION GEAR

[75] Inventor: Henri Leonard, Besancon, France

[73] Assignee: Micro-Mega, S.A., France

[21] Appl. No.: 108,171

[22] Filed: Dec. 28, 1979

Related U.S. Application Data

[63] Continuation-in-part of Ser. No. 867,098, Jan. 5, 1978, abandoned.

[30] Foreign Application Priority Data

Mar. 10, 1977 [FR] France ................. 77 07749

[51] Int. Cl.³ .......................... A61C 1/08; A61C 1/02
[52] U.S. Cl. ................................ 433/104; 433/126; 433/105; 74/801
[58] Field of Search ............. 433/105, 126, 104; 74/750 R, 789

[56] References Cited

U.S. PATENT DOCUMENTS

| | | | |
|---|---|---|---|
| 2,721,591 | 10/1955 | Criswell | 74/750 R |
| 2,780,944 | 2/1957 | Ondeck | 74/750 R |
| 3,324,553 | 6/1967 | Borden | 433/126 |
| 3,487,546 | 1/1970 | Beierlein et al. | 433/104 |
| 3,942,392 | 3/1976 | Page, Jr. et al. | 433/105 |
| 4,040,311 | 8/1977 | Page, Jr. et al. | 433/120 |

FOREIGN PATENT DOCUMENTS 1404063  8/1975  United Kingdom ............ 74/750 R Primary Examiner—Gene Mancene
Assistant Examiner—John J. Wilson
Attorney, Agent, or Firm—Robert E. Burns; Emmanuel J. Lobato; Bruce L. Adams

[57] ABSTRACT

A modular reduction gear for a dental handpiece comprises an input shaft coupled to the driving motor and provided with a pinion constituting the sun wheel of an epicyclic gear of which the planet carrier is rigid with the adjacent end of the output shaft transmitting the rotary motion to the dental instrument, the carrier supporting three planet pins having mounted thereon for free rotary motion three planet pinions meshing with the sun pinion and with a fixed toothed annulus clamped between the pair of sockets constituting the body of the handpiece.

7 Claims, 4 Drawing Figures

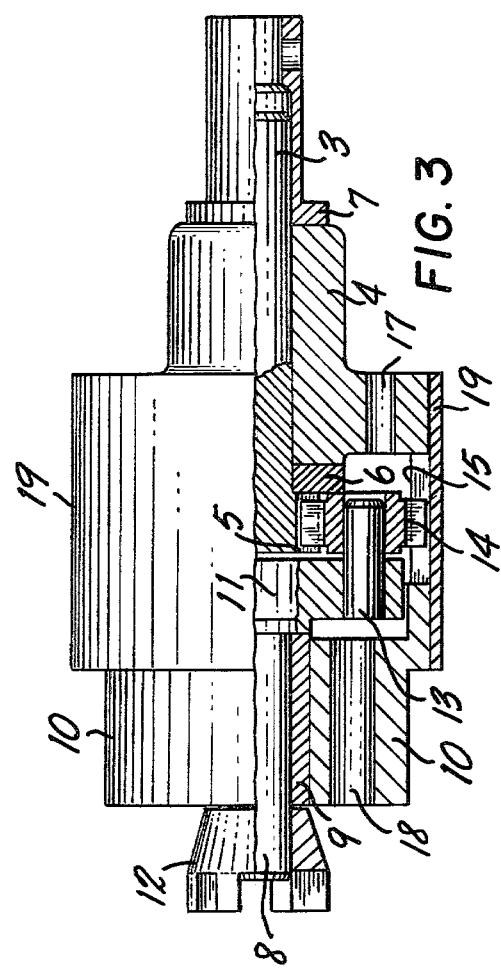
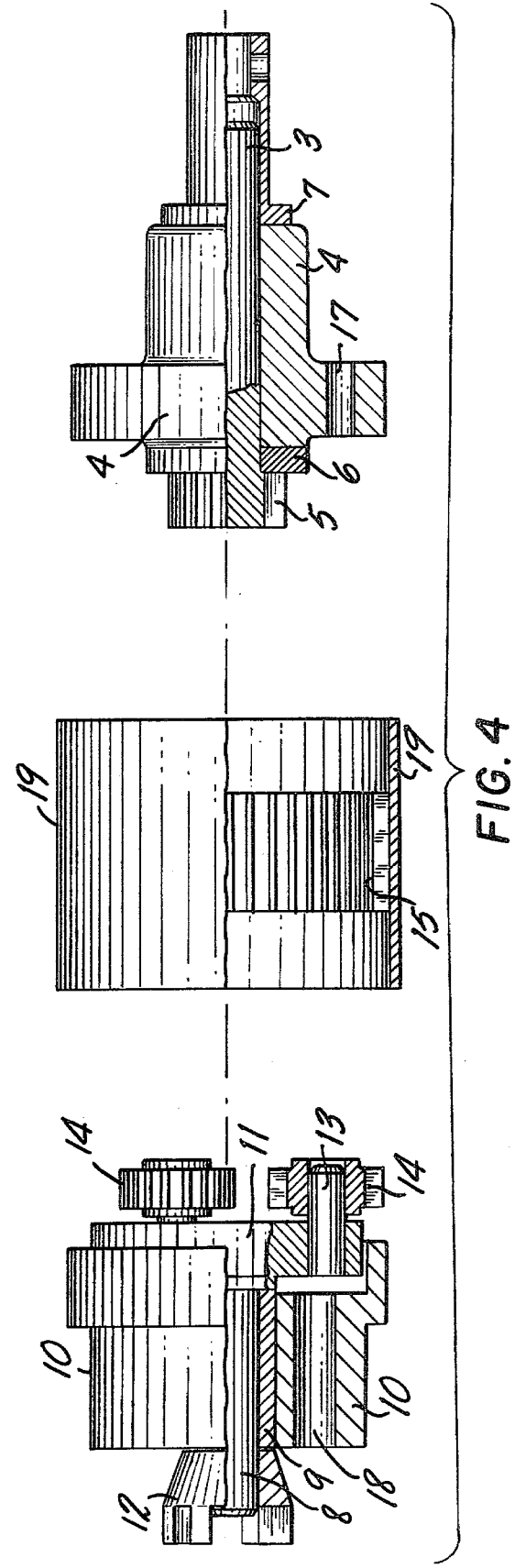

DENTAL HANDPIECE REDUCTION GEAR

This is a continuation-in-part of Ser. No. 867,098 filed Jan. 5, 1978, and now abandoned.

FIELD OF INVENTION

This invention relates to a reduction gear for dental hand tool holders or handpieces, of the type comprising an input shaft driven from the motor and an output shaft for transmitting the rotary motion to an instrument, in particular to a burr, both input and output shafts being mounted in mutual alignment within the body of the handpiece consisting of two sockets secured to each other.

DESCRIPTION OF THE PRIOR ART

Reduction gears are widely used in the field of dental handpieces whenever it is desired to increase the torque available at the instrument.

Thus for instance, a gear type reducer is known wherein the two registering ends of the two sections of the rotary longitudinal shaft carry respectively two pinions of different diameters which mesh respectively with a pair of pinions rigid with a transverse lay shaft having its axis perpendicular to the axis of the longitudinal shaft. To reduce the overall dimensions of the mechanism, one of the pinions rigid with one section of the longitudinal shaft is bell-shaped so that the larger toothed pinion rigid with the lay shaft can fit partially therein. These known devices are objectionable in that they are particularly cumbersome, notably in the axial direction.

DESCRIPTION OF THE INVENTION

It is the primary object of the present invention to provide a modular reduction gear constituting a substantial improvement over the prior art in that its overall dimensions are reduced considerably while affording a very regular rotational movement.

For this purpose, the reduction gear according to this invention is characterized in that the driving end of the input shaft is provided with a toothed sun pinion and that the driven end of the output shaft comprises a head supporting three planet pins parallel to the axis of the toothed pinion, said three planet pins being disposed at the vertices of an equilateral triangle and each having mounted thereon for free rotary motion a planet pinion, the three planet pinions meshing on the one hand with said central sun pinion which they surround and on the other hand, externally, with a fixed and internally toothed annulus surrounding in turn said planet pinions and secured between the two sockets constituting the body of said holder.

BRIEF DESCRIPTION OF THE DRAWING

FIG. 3 is a half-elevational, half-sectional view of the modular reduction gear disassembled from body of the dental handpiece, and FIG. 4 is a similar view but showing subassemblies of the reduction gear separated.

DESCRIPTION OF THE PREFERRED EMBODIMENT

Figures 1, 2:
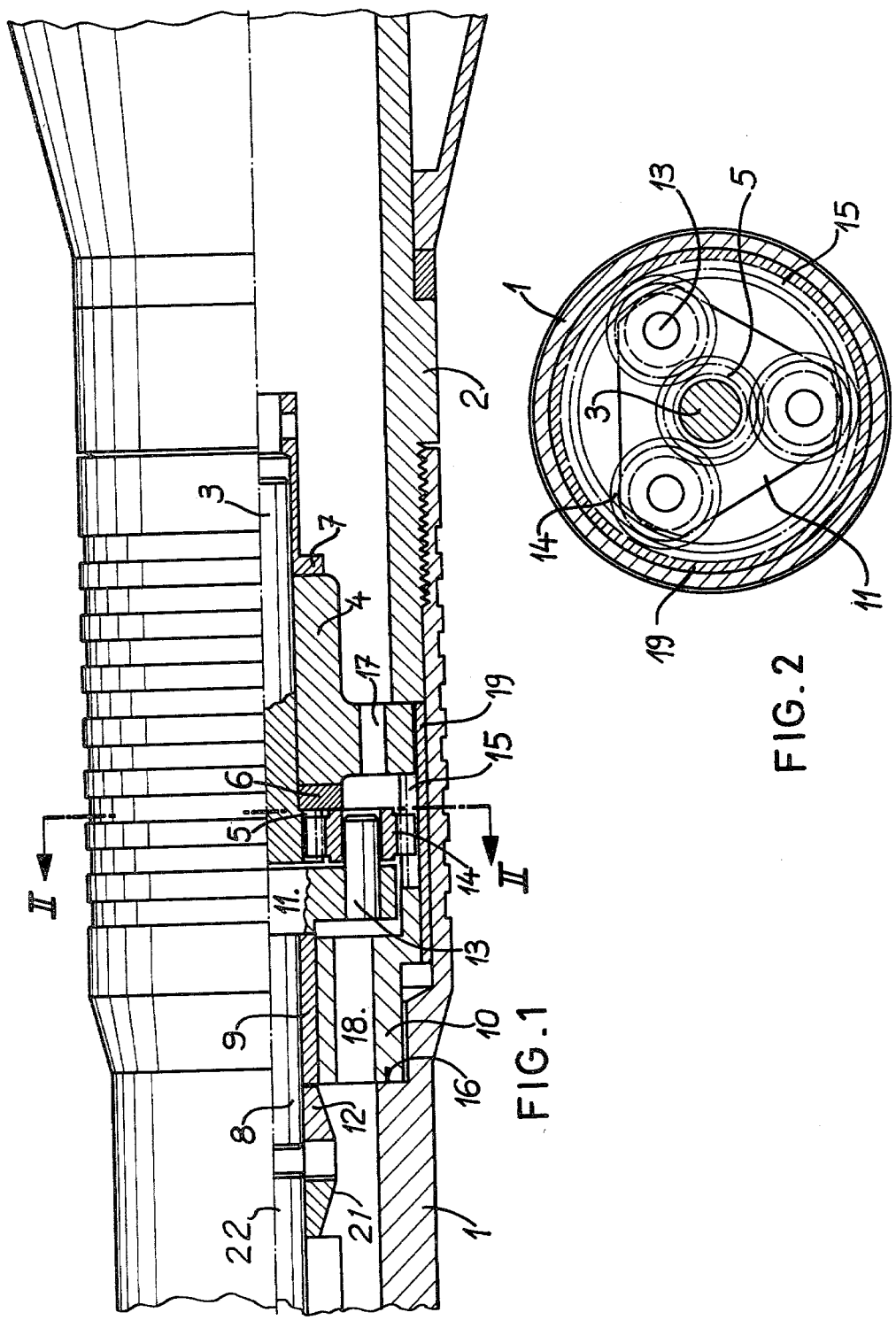
FIG. 1 is a half-elevation, half-sectional view of a dental handpiece according to this invention.
FIG. 2 is a section taken along the line I—I of FIG. 1.

Mounted for rotation in the body of the handpiece consisting of a front socket 1 screwed to a rear socket 2 is an input shaft 3 rotatably supported by a bearing 4. The head of shaft 3 is formed into a toothed pinion 5, a washer 6 force fitted on shaft 3 behind said pinion acting as an abutment member engaging the bearing 4. Force fitted on the opposite end of shaft 3 is a driving member 7 to which rotational motion is imparted from the motor (not shown), this member 7 also acting as an abutment member.

In axial alignment with input shaft 3 is an output shaft 8 rotatably mounted in a bearing 9 force fitted in a bearing support 10. The end of output shaft 8 which is adjacent the input shaft 3 carries a triangular, equilateral head or planet carrier 11 and the opposite end of shaft 8 has force fitted thereon a pinion 12 abutting the bearing 9. The pinion 12 engages with a pinion 21 fixed on the rear end of a shaft 22 which extends to the forward end of the handpiece. The head 11 of output shaft 8 carries three pins 13 parallel to the axis of said pinion 5 and disposed near the vertices of the equilateral triangle forming the head 11. Each pin 13 has mounted for free rotation thereon a planet pinion 14 meshing on the one hand internally with pinion 5 of input shaft 3 which acts as a sun pinion and on the other hand externally with an internally toothed annulus or ring gear 15 formed centrally of a sleeve 19 secured in the front socket 1 of the body of the handpiece. This toothed annulus 15 bears on the one hand against the support 10 abutting in turn an inner shoulder 16 of front socket 1, and on the other hand against the bearing 4 engaging in turn the end of the rear socket 2.

The device therefore comprises two easily interfitting sections, i.e. a first section consisting of input shaft 3, sun pinion 5, bearing 4 and driving member 7 all mounted in the rear socket 2, and a second section comprising output shaft 8, pinion 12, planet carrier 11 with its planet pinions 14, and support 10 with bearing 9 all mounted in the front socket 1 as shown. The planet pinions 14 on the planet carrier 11 are received in the sleeve 19, also mounted in the front socket 1, so as to mesh with the toothed annulus 15 and with the sun gear 5.

As illustrated in FIGS. 3 and 4, the modular reduction gear is removable from the body of the handpiece comprising front socket 1 and rear socket 2 (FIG. 3) and is separable into the two easily interfitting sections (FIG. 4). Thus one part of the modular assembly comprises the input shaft 3, bearing 4, driving member 7, sun pinion 5 and washer 6. The driving member 7 and the washer 6 force-fitted on the shaft 3 abut opposite ends of the bearing 4 to position the shaft 3 and pinion 5 axially relative to the bearing and to retain the parts in subassembled condition. The other part of the modular assembly comprises the output shaft 8, bearing 9, bearing support 10, planet carrier 11 fixed on the rear end of shaft 8, planet pinions 14 rotatably supported by pins 13 on the planet carrier 11 and a coupling pinion 12 force-fitted on the forward end of shaft 8. The planet carrier 11 and pinion 12 engage opposite ends of the bearing 9 to position the shaft 8 axially relative to the bearing 9 and to retain the parts of the subassembly in assembled condition. As seen in FIG. 4, the two subassemblies of the modular reduction gear are separable from the sleeve 19 with its ring gear 15. Moreover, the planet pinions 14 are removable from the pins 13 of the planet carrier 11. The several parts can thus be disassembled for inspection or replacement.

When the front socket 1 is unscrewed from the rear socket 2, the modular reduction gear assembly as illustrated in FIG. 3 is removable from the body of the handpiece and can thereupon be separated into the two sections and intermediate sleeve 19 as illustrated in FIG. 4. The parts are reassembled by reverse procedure. Thus the parts shown in FIG. 4 are assembled as illustrated in FIG. 3 and the resulting modular reduction gear assembly is fitted into the handpiece body comprising front socket 1 and rear socket 2 as shown in FIG. 1. It will be seen that the support 10 of the front section and the bearing 4 of the rear section fit into opposite ends of the intermediate sleeve 19 which in turn is received in the front socket 1. When the front socket 1 and the rear socket 2 are screwed together, the toothed annulus 15 formed centrally of the sleeve 19 is clamped between bearing 4 and bearing support 10 to position the toothed annulus 15 in mesh with the planet pinions 15 and to secure the toothed annulus 15 and sleeve 19 against axial displacement and rotation. With the modular reduction gear installed in the body of the handpiece as shown in FIG. 1, the driving member 7 is coupled with the motor (not shown) to drive the shaft 3 and thereby drive shaft 8 through the reduction gearing comprising sun gear 5, planet pinions 14 and toothed annulus 15. The pinion 12 on the forward end of shaft 8 engages with the pinion 21 on the rear end of shaft 22 to drive shaft 22.

It will be noted that the sleeve 19 is symmetrical in that the toothed annulus 15 is formed centrally within said sleeve. This arrangement is advantageous in that it greatly facilitates the assembling of the parts since there is no particular mounting direction to adhere to for inserting the sleeve 19 into the front socket 1. Holes 17, 18 are formed in bearing 4 and support 10 to permit the circulation of air or lubricating spray.

The above-described speed reducer operates as follows:

The input shaft 3 is rotatably driven from the motor (not shown) via driving member 7 and drives in turn through its pinion 5 the planet pinions 14 which, by meshing with and reacting against the fixed annulus 15 cause the carrier head 11 to revolve. If the sun pinion 5 and planet pinions 14 have the same diameter and twelve teeth each, and if the fixed annulus 15 has a diameter of three times that of sun pinion 5, and therefore 36 teeth, the output shaft 8 will be driven with a 1:4 gear ratio reduction. Of course, other reduction ratios may be contemplated by modifying the ratio of the diameters of the central or sun pinion, planet pinions and fixed annulus. With the constructions shown in the drawings, the toothed annulus 15 can be readily removed from the sleeve 19 when the front and rear sockets are disconnected. Moreover, the support 10, shaft 8, pinion 12 and head 11 with the planet pinions 14 can be removed as a unit. Also the pinion 5 is readily accessible for removal and replacement. Thus different gear ratios can be obtained by replacing the gears 5, 14 and 15 with gears of different sizes.

Pinion 12 may be engaged either by another pinion such as pinion 21 or by other coupling means for transmitting the rotary motion to the front section of the dental hand tool holder, which may be either a straight handpiece or a contraangle, as well known in the art.

This speed reducer may therefore advantageously be adapted to any type of dental handpiece.

Of course, various modifications and variations may be contemplated when carrying out the present invention in actual practice, as will readily occur to those conversant with the art, without inasmuch departing from the basic principles of the invention as set forth in the appended claims.

What is claimed is:

1. In a dental handpiece comprising a rear socket and a front socket removably connected to said rear socket, a removable modular reduction gear comprising two easily interfitting sections, namely:

a first section removably received in said rear socket and comprising a first bearing, a central input shaft rotatably supported by said bearing, means for retaining said input shaft against movement longitudinally of said bearing, means at the rear end of said shaft for rotationally driving said shaft in either direction of rotation, and a sun pinion on the front end of said input shaft, a second section removably received in said front socket and comprising a second bearing abutting a shoulder in said front socket, a central output shaft rotatably supported by said second bearing, a coupling member on the forward end of said output shaft and abutting the front end of said second bearing, a planet gear carrier fixed on the rear end of said output shaft and abutting the rear end of said second bearing, whereby said output shaft is retained by said coupling member and said planet gear carrier against movement longitudinally of said second bearing, and a plurality of freely rotatable planet gears carried by said planet gear carrier, and an intermediate sleeve received in said front socket and having an internal ring gear opposite ends of which are abutted by said first and second bearings to hold said sleeve against rotary and axial movement in position for engagement of said internal ring gear by said planet pinions which mesh with said internal ring gear and with said sun pinion on said input shaft when said front socket is connected to said rear socket with said first and second sections of said modular reduction gear interfitting, said first and second sections being removable from said rear socket and front socket respectively when said front socket is disconnected from said rear socket.

2. A dental handpiece according to claim 1, in which said internal ring gear is located centrally between opposite ends of said intermediate sleeve, whereby said sleeve is reversible end-for-end when said reduction gear is assembled.

3. A dental handpiece according to claim 1, in which said coupling member on the forward end of said output shaft in a pinion engageable with a pinion on an axially aligned third shaft extending toward the front end of said front socket.

4. A dental handpiece according to claim 1, in which axially extending bores are provided in said first and second bearings for the circulation of lubricating or cooling fluid therethrough.

5. A dental handpiece according to claim 1, in which the diameter of said planet gears is equal to the diameter of said sun gear.

6. A dental handpiece according to claim 1, in which there are three planet gears and in which said planet carrier has the form of an equilateral triangle and has three bearing pins disposed at the apices of an equalateral triangle and rotatable supporting said planet gears.

7. A dental handpiece according to claim 1, in which adjacent end portions of said first and second bearings are received in opposite end portions of said intermediate sleeve and abut said internal ring gear, while opposite ends of said first and second bearings abut annular shoulders of said rear socket and front socket respectively.

* * * * *